United States Patent [19]

Enei et al.

[11] 3,969,188

[45] July 13, 1976

[54] METHOD OF PRODUCING GUANOSINE BY FERMENTATION

[75] Inventors: Hitoshi Enei, Zushi; Katsuaki Sato; Yasuo Anzai, both of Kawasaki; Yoshio Hirose, Fujisawa, all of Japan

[73] Assignee: Ajinomoto Co., Inc., Tokyo, Japan

[22] Filed: Oct. 24, 1974

[21] Appl. No.: 517,631

[30] Foreign Application Priority Data
Oct. 24, 1973 Japan.............................. 48-119749

[52] U.S. Cl............................................. 195/28 N
[51] Int. Cl.².......................................... C12D 13/06

[58] Field of Search.................................. 195/28 N

[56] References Cited
UNITED STATES PATENTS
3,575,809   4/1971   Shiro et al. ........................ 195/28 N

*Primary Examiner*—Alvin E. Tanenholtz
*Attorney, Agent, or Firm*—Cooper, Dunham, Clark, Griffin & Moran

[57] ABSTRACT

Method for producing guanosine by culturing a guanosine-producing mutant of the genus Bacillus which requires adenine for growth, and is resistant to at least one sulfa drug.

5 Claims, No Drawings

METHOD OF PRODUCING GUANOSINE BY FERMENTATION

This invention relates to a method of producing guanosine by fermentation.

Guanosine has a great use for producing sodium salt of guanosine 5'-monophosphate which is useful as a seasoning agent. It is known that a mutant of Bacillus subtilis resistant to 8-azaguanine and requiring adenine for growth produces guanosine in the culture medium in which it grows (J. Gen. Appl. Microbiol., 15, 399–411 (1969)).

It has now been found that remarkably higher amount of guanosine is produced, when it is compared with the known method, by culturing in a culture medium a mutant of Bacillus which is resistant to at least one compound selected from sulfadrugs, and which requires adenine for growth.

The mutants are derived from the parent strains by exposing mutagenic doses of ionizing radiation (ultra-violet lights, X-rays, gammarays) or of chemical agents (sodium nitrate, N-methyl-N'-nitro-N-nitrosoguanidine, diethyl sulfate), and by screening the treated parent strains for mutants having the desired properties. Adenine-requiring mutants are isolated by the replication method, and mutants resistant to sulfa drugs, are identified by their ability of growing vigorously on otherwise conventional media containing enough of the compounds to be resisted to suppress growth of the parent strains.

Resistance is determined by comparing the relative growth of the mutant in the presence of sulfa drugs with that of parent strain, relative growth being the ratio of growth on a medium containing sulfa drugs to growth on a medium free from sulfa drugs.

The sulfa drugs used in this invention contain the group:

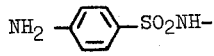

and have anti-microbial action which is suppressed at least in part by p-aminobenzoic acid.

Presently known sulfa drugs having the features mentioned above are sulfapyridine, sulfathiazole, sulfadiazine, sulfaguanidine, sulfamethazine, sulfamerazine, sulfadimethoxine, sulfamethomidine, sulfamethoxypuridazine, sulfisomidine, sulfisoxazole, acetosulfamine, sulfamethizole, sulfaethidole, sulfapyrazine, irgafen, irgamide, sulfanylamide, sulfisomezole, and sulfaphenazole.

It has been found that mutants which resist one sulfa drug also resist usually other sulfa drugs.

Mutant which is resistant further to 8-azaguanine usually produce more increased amount of guanosine. Mutant resistant to 8-azaguanine is resistant also to other purine analogues such as 8-azaxanthine, 8-azaadenine, thiainosine, 6-mercaptopurine, 6-chloropurine, 6-aminopurine, 2-amino-6-mercaptopurine, 4-hydroxythiazolepyrimidine, 6-mercapto-8-hydroxypurine, and 6-methyl-4-nitro-5-imidazole thiopurine.

The most effective guanosine producing mutants found so far (and the compounds employed in screening them, and then to which the mutants resist) are as follows:

Bacillus subtilis AJ 3617 (FERM-P 2313) (sulfaguanidine)

Bacillus subtilis AJ 3618 (FERM-P 2314) (8-azaguanine, sulfamerazine)

The culture media in which the mutants of the invention produce guanosine are largely conventional. They must contain sources of assimilable carbon and nitrogen and adenine, and should further contain inorganic ions and minor organic nutrients. Suitable carbon source may be glucose, fructose, sucrose, starch hydrolyzate and molasses. Nitrogen may be derived from nitrates, ammonium salts, ammonium hydroxide, urea, and like inorganic and organic compounds.

Aerobic conditions are maintained by aeration and/or agitation, and pH is held between 5 and 9 for good yields. When ammonia is used for pH control, it may also serve as a nitrogen source. The guanosine concentration in the broth reaches its maximum within 2 to 7 days if the fermentation is carried out at 24° to 37°C.

The guanosine accumulated in the fermentation broth can be recovered by conventional methods, such as removing cells by filtration or centrifuging, or passing the broth over an ion exchange resin.

Microorganisms identified by FERM-P numbers are available from the Fermentation Research Institute of the Agency of Industrial Science & Technology, Chiba-shi, Chiba-ken, Japan.

The following Examples further illustrate the invention.

EXAMPLE 1

Resistance of each mutant to the compounds listed in Tables was tested as follows:

An aqueous medium was prepared to contain, per deciliter, 0.02 g $M_gSO_4 \cdot 7H_2O$, 0.05 g sodium citrate, 0.1 g L-glutamic acid, 2.5 g glucose, 0.5 g $NH_4Cl$, 0.4 g $KH_2PO_4$, 1 mg $FeSO_4 \cdot 7H_2O$, 1 mg $MnSO_4 \cdot 4H_2O$, 100 μg vitamin $B_1$, 10 mg adenine and 0.2 g caseinhydrolyzate (pH 7.0). The aqueous medium was further added with each of compounds listed in Tables 1 to 3, and placed (total volume 3 ml) in test tubes. Each tube was inoculated after sterilization with 0.05 ml of cell suspension containing $10^6$ cells/ml, and shaken at 34°C for 24 hours. Growth was determined by measuring turbidity of culture broth. Results are shown in Tables 1 to 3.

Table 1

| Sulfaguanidine γ/cc | Relative Growth | |
|---|---|---|
| | AJ 3483 | AJ 3617 |
| 0 | 100 | 100 |
| 10 | 20 | 93 |
| 20 | 10 | 86 |
| 50 | 5 | 80 |
| 100 | 2 | 55 |
| 300 | 0 | 32 |
| 500 | 0 | 5 |
| 1000 | 0 | 2 |

Table 2

| Sulfamerazine γ/cc | Relative Growth | |
|---|---|---|
| | AJ 3483 | AJ 3618 |
| 0 | 100 | 100 |
| 10 | 26 | 90 |
| 20 | 10 | 90 |
| 50 | 2 | 85 |
| 100 | 0 | 60 |
| 300 | 0 | 20 |
| 500 | 0 | 8 |
| 1000 | 0 | 0 |

Table 3

| 8-Azaguanine γ/cc | Relative Growth | |
| --- | --- | --- |
| | AJ 3483 | AJ 3618 |
| 0 | 100 | 100 |
| 50 | 50 | 100 |
| 100 | 18 | 92 |
| 300 | 2 | 40 |
| 500 | 0 | 15 |
| 1000 | 0 | 0 |
| 2000 | 0 | 0 |

EXAMPLE 2

Each microorganism listed in Table 4 was cultured with shaking at 34°C for 16 hours in an aqueous culture medium containing 2 g/dl glucose, 0.5 g/dl yeast extract, 0.1 g/dl NaCl, 20 mg/dl adenine, 4 ml/dl soy-protein-acid hydrolyzate ("MIEKI"), 0.02 g/dl $KH_2PO_4$ and 0.04 g/dl $MgSO_4.7H_2O$.

An aqueous fermentation medium was prepared to contain, per deciliter, 8 g glucose, 1.5 g $NH_4NO_3$, 0.02 g $KH_2PO_4$, 0.04 g $MgSO_4.7H_2O$, 0.2 mg ferrous ion, 0.2 mg manganese ion, 0.2 g $CaCl_2.2H_2O$, 0.1 g RNA (separated from yeast), 4 ml soyproteinacid hydrolyzate and 3 g $CaCO_3$ (separately sterilized), adjusted to pH 7.0 and sterilized with steam.

20 ml Batches of the fermentatin medium in 500 ml flasks were inoculated each with 1 ml of the previously prepared seed cultures.

The fermentation was carried out at 34°C with shaking for 72 hours. The amounts of guanosine in the fermentation broths was determined by paper-chromatography, and the results are shown in Table 4.

Table 4

| Microorganism | | | Guanosine accumulated (g/l) |
| --- | --- | --- | --- |
| Bacillus | subtilis | AJ 3617 | 8.3 |
| " | " | AJ 3618 | 9.5 |
| " | " | AJ 3483 | 1.8 |

*Bacillus subtilis* AJ 3483 is adenine-requiring and guanosine producing mutant from which the mutants in this invention were induced.

1.5 Liter of the fermentation broth of AJ 3618 were prepared by the analogous manner as above. Cells were separated from the broth by filtration, and thereafter guanosine was isolated with an anion exchange resin. 14.3 G of crude guanosine crystalline were precipitated by adding acetone to the eluate.

What is claimed is:

1. A method for producing guanosine which comprises culturing a guanosine-producing mutant of the genus Bacillus under aerobic conditions in an aqueous culture medium until guanosine accumulates in the medium, and recovering accumulated guanosine therefrom; the mutant being characterized by a requirement for adenine for growth and by being resistant to at least one sulfa drug at a level of 100 gamma per cubic centimeter, said sulfa drug containing the group

and having anti-microbial action which is suppressed at least in part by p-aminobenzoic acid.

2. A method as set forth in claim 1, wherein said mutant is resistant to 8-azaguanine.

3. A method as set forth in claim 1, wherein said sulfa drug is sulfaguanidine or sulfamerazine.

4. A method as set forth in claim 1, wherein said mutant is a mutant of *Bacillus subtilis*.

5. A method as set forth in claim 1, wherein said mutant is *Bacillus subtilis* FERM-P 2313 or *Bacillus subtilis* FERM-P 2314.

* * * * *